United States Patent [19]

Wheldon et al.

[11] 4,112,736
[45] Sep. 12, 1978

[54] GAS DETECTOR

[75] Inventors: Alfred G. Wheldon; Ernest D. Harris, both of Dagenham Dock, England

[73] Assignee: The Distillers Company (Carbon Dioxide) Ltd., Reigate, England

[21] Appl. No.: 759,900

[22] Filed: Jan. 17, 1977

[51] Int. Cl.² .............................................. G01N 7/10
[52] U.S. Cl. ......................................................... 73/23
[58] Field of Search ............... 73/23, 19; 55/158, 270; 251/9

[56] References Cited

U.S. PATENT DOCUMENTS

| 1,825,024 | 9/1931 | Tandberg | 73/23 |
| 2,045,379 | 6/1936 | Bennett | 73/23 |
| 2,561,414 | 7/1951 | Potts | 73/23 |
| 3,411,534 | 11/1968 | Rose | 251/9 |
| 3,438,241 | 4/1969 | McKinley | 73/19 |
| 3,450,152 | 6/1969 | Ouellette | 251/9 |
| 3,871,228 | 3/1975 | Weiss | 73/19 |
| 3,926,561 | 12/1975 | Lucero | 73/23.1 |
| 3,977,232 | 8/1976 | Hickam et al. | 73/19 |

Primary Examiner—Stephen A. Kreitman

[57] ABSTRACT

A detector for detecting the presence of a particular gas in a mixture of gases comprises a space bounded in part by a membrane which is preferentially permeable to the particular gas and bounded in part by a thin flexible diaphragm. The diaphragm is arranged to control flow through a nozzle to which, in use, a gas is supplied at a steady pressure, and means are provided to supply the mixture of gases to one face of the membrane. In use, when the particular gas is present in the mixture being supplied to the one face of the membrane the particular gas permeates through the membrane from the one face to change the pressure in the space and cause the diaphragm to bow and produce a change of pressure in the supply of gas upstream from the nozzle. The change in pressure in the supply of gas upstream from the nozzle constitutes a pneumatic signal indicating the presence of the particular gas in the mixture. The membrane and the thin flexible diaphragm may be formed from the same piece of material.

27 Claims, 5 Drawing Figures

GAS DETECTOR

BACKGROUND OF THE INVENTION

1. Field of the Invention

This invention relates to a detector for detecting the presence of a particular gas in a mixture of gases and in particular to a gas detector which utilizes diffusion through a piece of material which exhibits differential permeability.

2. Prior Art

Our earlier British patent specification No. 1452574 published on the 13th Oct., 1976 describes a simple gas detector for detecting sudden and abrupt changes in the concentration of a particular gas in a mixture of gases. The detector is intended to be used to initiate the collection of carbon dioxide evolved from a fermentation process when the concentration of carbon dioxide in the mixture of gases evolved from the fermentation process exceeds a predetermined value. This detector is robust and reliable in use but it can only be used in situations where there is a sudden and large change in the concentration of the particular gas to be detected.

SUMMARY OF THE INVENTION

According to the present invention a detector for detecting the presence of a particular gas in a mixture of gases comprises a space bounded in part by a membrane which is preferentially permeable by the particular gas and bounded in part by a thin flexible diaphragm movement of which is arranged to control flow through a nozzle to which, in use, a gas is supplied at a steady pressure, and means to supply the mixture of gases to one face of the membrane, the arrangement being such that, in use, when the particular gas is present in the mixture it permeates through the membrane from the one face to change the pressure in the space and cause the diaphragm to bow and produce a change of pressure in the supply of gas upstream from the nozzle, the change in pressure constituting a pneumatic signal indicating the presence of the particular gas in the mixture.

The means to supply the mixture of gases to the one face of the membrane may include a chamber which is partly bounded by the one face of the membrane and has an inlet for the mixture of gases and an outlet. In this arrangement when the particular gas is present in the mixture it permeates through the membrane from the one face into the space to increase the pressure within the space and cause the diaphragm to bow outwards away from the space and produce a change of pressure in the supply of gas upstream from the nozzle. This provides a pneumatic signal which indicates the presence of the particular gas.

Alternatively, the means to supply the mixture of gases to one face of the membrane may include a valve-controlled inlet and outlet for the space to allow a sample of the mixture of gases to be introduced into the space so that, in use, when the particular gas is present in the mixture it permeates through the membrane from the one side which partly bounds the space, out of the space to reduce the pressure in the space and cause the diaphragm to bow inwards into the space and produce a change of pressure in the supply of gas upstream from the nozzle, the change in pressure constituting a pneumatic signal which indicates the presence of the particular gas.

The thin flexible diaphragm is preferably arranged to interfere directly with the flow of gas through the nozzle but the diaphragm may control flow of gas through the nozzle through an intermediate member, for example the operating member of a valve.

The membrane which is preferentially permeable by the particular gas may be flexible and in this case the thin flexible diaphragm and the membrane are preferably formed by the same piece of material. When the thin flexible diaphragm and the membrane are formed by the same piece of material the space partly bounded by the membrane is preferably formed by a chamber having a valve-controlled inlet and outlet and having one of its faces formed by the single piece of material which forms both the membrane and the diaphragm, the nozzle being outside the chamber and being arranged so that the gas flowing through the nozzle impinges on the outside of the material forming both the membrane and the diaphragm.

When the membrane is made from a material which is not flexible it may be formed as a composite structure and include a diaphragm portion which is made from a different and flexible material. This composite structure of the membrane and the diaphragm preferably forms one face of the chamber with the nozzle arranged adjacent the flexible diaphragm portion in a similar way to the case of a flexible membrane. However, when the membrane is not flexible the space may include a further chamber which is partly bounded by a thin flexible diaphragm and, in this case the nozzle is arranged outside the space and adjacent the thin flexible diaphragm.

Examples of the particular gas which may be detected by a detector in accordance with this invention include carbon dioxide, water vapour and hydrogen. To detect these gases membranes made from silicone rubber, cellulose acetate and palladium respectively, are preferably used. A silicone rubber membrane is particularly effective when it is also used as the thin flexible diaphragm to directly control the flow of gas through the nozzle. Palladium and cellulose acetate are not sufficiently flexible to enable to sensitive detector to be made and it is therefore preferred that a detector having a palladium or cellulose acetate membrane includes a separate flexible diaphragm made from a different material.

When the means to supply the mixture of gases to the one face of the membrane includes a chamber which has an inlet and an outlet and which is outside the space so that, when the particular gas is present in the mixture, it permeates through the membrane from the one face into the space to increase the pressure within the space and cause the diaphragm to bow outwards away from the space, the nozzle preferably forms part of the inlet into the chamber and the detector preferably includes means for supplying the mixture of gases through the nozzle and into the first chamber at a steady pressure. In this case the space preferably includes an inlet having an inlet valve and an outlet having an outlet valve so that a supply of gas may be passed through the space to purge it. The detector preferably includes a timing device which is arranged to control the inlet and outlet valves of the space to purge the space at predetermined intervals. The increase in pressure in the space during the predetermined time interval gives an indication of the concentration of the particular gas in the gas mixture passing through the chamber. The inlet and outlet valves of the space are preferably arranged so that for each purge cycle first the outlet valve is opened, then the inlet valve is opened to allow the purging gas to pass through the space and out of the outlet valve, then the inlet valve is closed and finally the outlet valve is closed. This sequence of operation for the valves ensures that the pressure within the space at the beginning of each predetermined time interval is that of the surrounding atmosphere.

Alternatively, when the means to supply the mixture of gases to one face of the membrane includes a valve-controlled inlet and outlet for the space and means to supply a sample of the mixture of gases into the space so that, in use, when the particular gas is present in the mixture it permeates through the membrane which partly bounds the space out of the space to reduce the pressure in the space and cause the diaphragm to bow inwards into the space, the nozzle is preferably arranged so that when the pressure within the space is the same as that outside, the diaphragm is located against the nozzle and so causes maximum interference with the flow of gas through the nozzle. In this way, when the particular gas is present in the mixture and it permeates through the membrane from the one side to reduce the pressure in the space it causes the diaphragm to bow inwards into the space and so reduce the interference of the flow of gas through the nozzle by the diaphragm leading to a reduction in the pressure of the gas upstream from the nozzle. Preferably the means to supply the mixture of gases to one face of the membrane also includes a pump which is arranged to flush the space with a sample of the gas mixture when the valve-controlled inlet and outlet to the space are opened. The detector preferably includes a timing device which is arranged to control the inlet and outlet valves of the space to flush the space through with a fresh sample of the gas mixture at predetermined intervals. The inlet and outlet valve of the space are preferably arranged so that for each flushing cycle first outlet valve is opened, then the inlet valve is opened to allow the gas mixture to pass through the space and out of the outlet valve, then the inlet valve is closed, and finally the outlet valve is closed. In this way the pressure within the space at the start of each cycle is the same as the pressure outside the space.

The sensitivity of the detector is improved if the size of the portion of the thin flexible diaphragm, or the portion of the membrane when they are made of the same piece of material, that is capable of bowing into or out of the space is reasonably small when compared to the total surface of the space. This can be achieved very simply by choosing the size of the diaphragm when a separate diaphragm is used and it may be achieved by including a rigid porous support covering parts of the membrane when the membrane and the diaphragm are formed of the same piece of material. The change of pressure in the space during the predetermined time interval gives an indication of the concentration of a particular gas in the gas mixture. The detector may include a pressure-responsive electrical switch upstream from the nozzle which responds to the change in pressure of the gas upstream from the nozzle when the diaphragm moves away from the nozzle and in this case the detector will merely give an indication if the concentration of the particular gas in the gas mixture exceeds a predetermined level. Alternatively, the detector may include a pressure gauge upstream from the nozzle so that an indication of the concentration of the particular gas in the gas mixture is given. The detector preferably includes a further valve arranged to isolate the pressure switch or the pressure gauge and this further valve is arranged to open before the outlet valve of the space is opened and to close once again immediately before the outlet valve of the second space is opened. The further valve maintains the pressure switch or gauge in the same state during the following cycle as existed at the end of the previous cycle and then allows the pressure in the switch or gauge to be re-adjusted at the end of the following cycle. In this way the pressure switch or gauge gives a continual indication of the concentration of the particular gas, and this indication is updated with each cycle of the detector. Preferably the timing device is a servo motor controlling all the valves through a series of cams.

The detector may include a pressure controller, for example a water bubbler to control the pressure of the supply of the gas to the nozzle. The detector may include a diaphragm pump to supply the gas mixture to the nozzle and it has been found that when a small, rapidly oscillating diaphragm pump is used to supply the gas to the nozzle, it is unnecessary to provide any further active means to control the pressure of the gas supply since the absolute delivery pressure of such a pump is substantially constant. Preferably a restriction is included in the supply line to reduce the maximum flow rate of the gas and smooth out and steady the delivery from the pump.

The atmosphere on the other side of the membrane with which the mixture of gases is compared is often formed by the "mixture of gases" without the particular gas to be detected. This situation may be arranged by treating the atmosphere on the other side of the membrane with a chemical which absorbs the particular gas to be detected. However, this is not preferred. The atmosphere outside the space may be formed by a gas which differs from any of those present in the mixture of gases or it may be formed by a combination of two or more such gases. When the detector is used to detect any build-up of the particular gas in air, for example in air surrounding a store of the particular gas, then it is convenient to use fresh air taken from a position remote from the store as the atmosphere on the other side of the membrane. An alternative in such a case would be to provide an atmosphere of nitrogen on the other side of the membrane. When it is required that the detector gives an indication of the absolute concentration of the particular gas the atmosphere on the other side of the membrane should be entirely free of the particular gas. However, when it is merely required to measure an increase in the concentration of a particular gas, the atmosphere on the other side of the membrane may contain a constant, known proportion of the particular gas and so only respond when a change in the concentration of the particular gas occurs in the mixture being examined.

A gas detector in accordance with this invention and including a silicone rubber membrane and a pressure switch, is particularly effective when it is used to detect the presence of carbon dioxide in, for example, a cellar or other carbonated beverage store where cylinders of carbon dioxide are kept. Carbon dioxide cylinders are widely used to pressurise kegs of beer and other carbonated beverages and since carbon dioxide is more dense than air, when a leakage occurs from one of the cylinders of carbon dioxide, the concentration of carbon dioxide builds up to an extent where it is dangerous for a person to enter the store. This is particularly true when the store is in a cellar and the detector in accordance with this invention gives a warning when the concentration reaches a dangerous level.

If there is a very large difference between the humidity of the sample being examined and the humidity of the atmosphere on the other side of the membrane, for example the sample taken from a cellar and that of the surrounding fresh air, the effects of a difference in the concentration of carbon dioxide between the two will, to some extent, be masked by this large difference in humidity. The silicone rubber membrane is permeable by water vapour as well as by carbon dioxide so it will allow some water vapour to permeate through it in this case. This problem may be overcome by drying the sample and the fresh air used as the atmosphere on the other side of the membrane, but preferably the detector includes a humidity exchanger formed by an additional chamber divided into two parts by a membrane made from cellulose acetate. The gas mixture passing through one side of the additional chamber and the gas to be used as the atmosphere on the other side of the membrane passing in counter-current through the other side of the additional chamber. With the detector in accordance with this invention it is not necessary to dry both gas streams but merely ensure that the humidity of both samples in similar. The ratio of the permeability of cellulose acetate by water vapour to that by carbon dioxide is of the order of 1000:1 so that there is effectively no transfer of carbon dioxide from the sample gas mixture to that of the atmosphere used on the other side of the membrane.

Various other preferred features of this invention will become apparent upon reference to the accompanying drawings and the following description.

DESCRIPTION OF THE PREFERRED EMBODIMENTS

Figure 1:
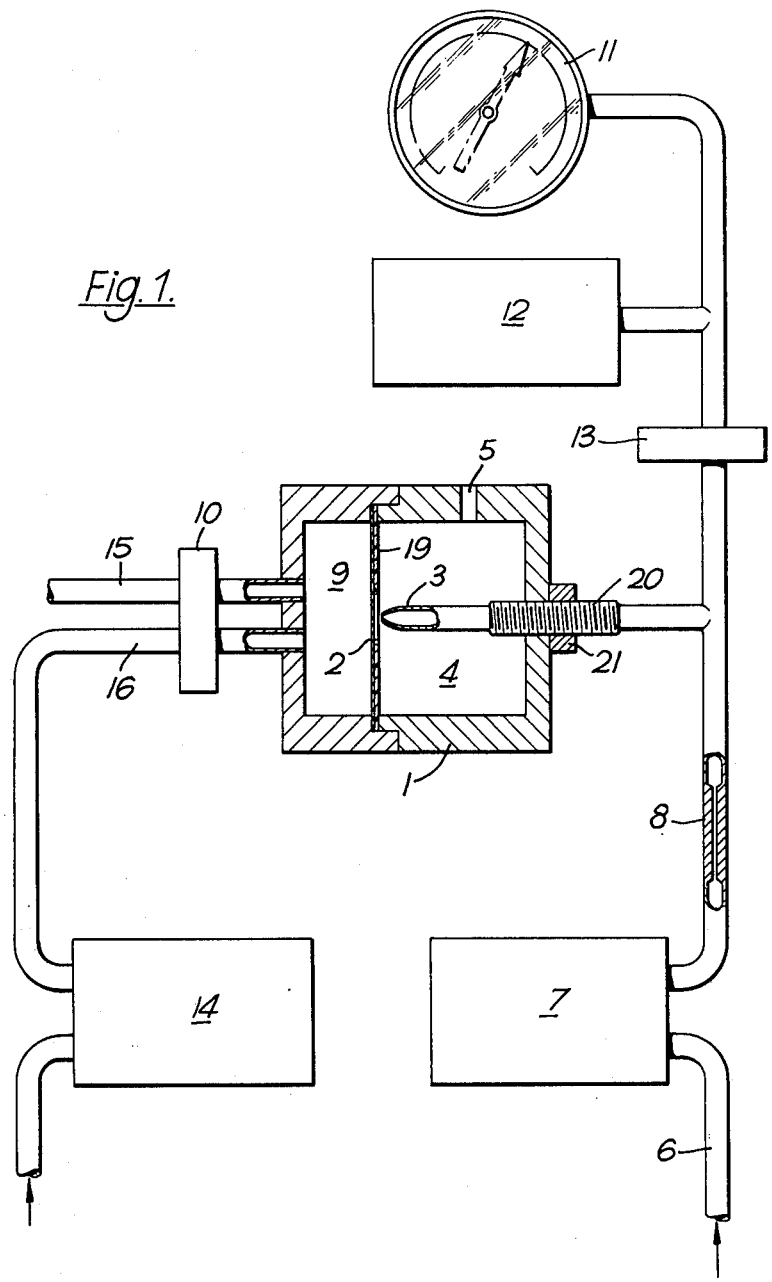
FIG. 1 is a somewhat schematic diagrammatic and partly sectioned diagram of a first example of a detector in accordance with this invention.
Figure 2:
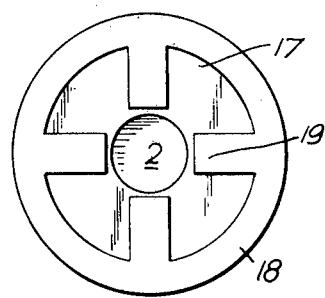
FIG. 2 shows the membrane and its support.
Figure 3:
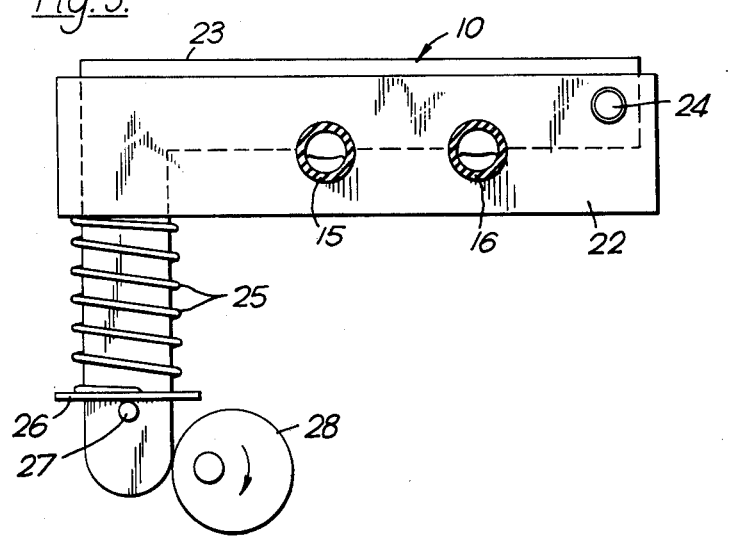
FIG. 3 is a side elevation of a double pinch valve used in a detector in accordance with this invention.
Figure 4:
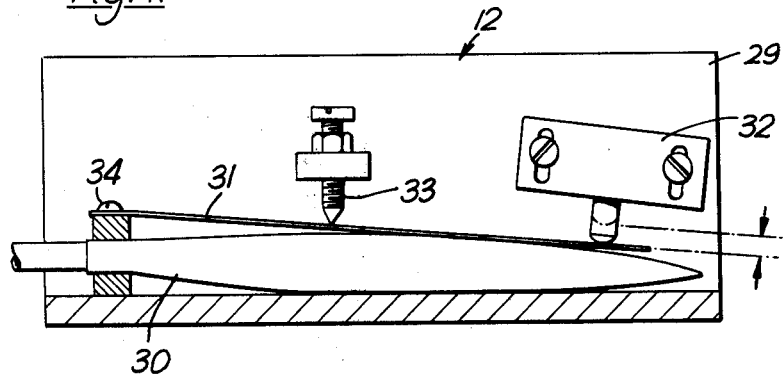
FIG. 4 is a longitudinal section through a pressure switch used in accordance with this invention; and, FIG. 5 is a partly sectioned somewhat diagrammatic view of a second example of gas detector in accordance with this invention.

The first example of a gas detector shown in FIGS. 1 to 4 is primarily intended to be used to detect an increase in the concentration of carbon dioxide present in the cellar of a public house. The detector includes a cylindrical housing 1 which is divided into two chambers by a membrane 2 made from silicone rubber sheeting having a thickness of the order of 0.002 inch. A nozzle 3 in a first chamber 4 of the housing 1 is located adjacent the membrane 2. A vent outlet 5 is provided in the wall of the first chamber 4. A sample of the mixture of gases to be examined, which in this case is drawn from the cellar, is drawn through a tube 6 by a diaphragm pump 7 and is then passed through a restriction 8 and then to the nozzle 3. The sample passes into the first chamber 4 and out through the vent outlet 5. The second chamber 9 is closed to the atmosphere by a pair of pinch valves 10.

When the concentration of carbon dioxide in the sample passing through the first chamber 4 is greater than the concentration of carbon dioxide in the second chamber 9, carbon dioxide permeates through the membrane 2 from the first chamber into the second chamber causing the pressure in the second chamber to increase. The rate of increase in pressure in the second chamber is dependent on the difference in the concentration of carbon dioxide in the first and second chambers. This increase causes the membrane 2 to bow from the second chamber 9 into the first chamber 4 and throttle the flow of gas through the nozzle 3. This increases the pressure in the tubing upstream from the nozzle 3. A pressure gauge 11 and a pressure switch 12 are connected through a pinch valve 13 to the tubing upstream from the nozzle 3, between it and the restriction 8. When the valve 13 is open the gauge 11 will give an indication of the pressure in the tubing upstream of the nozzle 3, and thus an indication of the concentration of carbon dioxide in the atmosphere of the cellar.

The detector is usually mounted out of the cellar and frequently at the top of the stairs leading down into the cellar. In this case a second diaphragm pump 14 draws air from outside a casing containing the detector and hence from the atmosphere outside the cellar, the diaphragm pump 14 supplies it to the inlet side of the pair of pinch valves 10. If the detector is mounted within the cellar or, in another situation located adjacent the region from which a sample is being taken, the gas drawn into the inlet of the diaphragm pump 14 must be drawn from a position remote from the cellar or from a position remote from the sample region. When the detector is not used for this purpose a sample of reference gas may be drawn into the inlet of the diaphragm pump 14.

The operation of the pinch valves 10 and 13 is controlled by a servo-motor (not shown) operating rotary cams which move the closure members of the pinch valves 10 and 13. The servo-motor is arranged so that it regularly opens a vent outlet tubing 15 from the second chamber 9 and then opens an inlet tubing 16 leading from the diaphragm pump 14 into the second chamber 9 to allow a purge gas to pass through the second chamber 9. The servo-motor then closes the inlet tubing 16 to the second chamber 9 and subsequently closes the vent outlet tubing 15 to once again isolate the second chamber 9 from the atmosphere. Before the servo-motor opens the vent outlet tubing 15 it opens the pinch valve 13 to bring the pressure switch 12 and the pressure gauge 11 into contact with the pressure upstream from the nozzle 3. Immediately before the servo-motor opens the vent outlet tubing 15 it closes the pinch valve 13 once again and thus the pressure gauge 11 gives a continuous reading corresponding to the maximum pressure achieved upstream from the nozzle 3 in each operating cycle of the detector.

The membrane 2 is very flexible and to make the detector more sensitive it is partly covered by an annular ring 17 of porous material, for example filter paper, and a ring 18 having radially extending fingers 19 extending inwards from its periphery. This is shown most clearly in FIG. 2. The fingers 19 and the ring 17 support the majority of the membrane 2 so that when the pressure within the second chamber 9 increases only the small central unsupported area of the membrane 2 is free to move in an attempt to normalise the increase in the pressure inside the second chamber 9. Consequently the membrane responds more rapidly and thus the detector is more sensitive. The position of the nozzle 3 is adjustable and the nozzle includes a screw-threaded spindle 20 so that it is movable axially into and out of the first chamber 4. The nozzle 3 is locked in position by a lock nut 21.

In this example the membrane and the diaphragm are formed by the same piece of material, the silicone rubber membrane 2, and the space bounded in part by the membrane and the thin flexible diaphragm is represented by the second chamber 9 and the tubings 15 and 16 in between the pinch valves 10 and the second chamber 9.

The pair of pinch valves 10 comprise a carrier 22 having a U-shaped cross-section, a cranked bar 23 located between the upstanding limbs of the U-shaped carrier 22 and silicone rubber tubing 15 and 16. When the tubings 15 and 16 are pinched between the bar 23 and the carrier 22 and their bores are closed, one end of the bar 23 is connected to the carrier 22 by a pivot 24 and the cranked free end of the operating member 23 is biased into the closed position by a spring 25 arranged and acting between the carrier 22 and a washer 26 which is fixed on to the bar 23 by a pin 27. A cam 28 driven by the servo-motor bears against the free end of the cranked operating member 23. As the cam rotates the operating member 23 pivots about the pivot 24 and as the tubing 15 is further away from the pivot than the tubing 16 the bore through the tubing 15 will be opened before the bore through the tubing 16 is opened and subsequently as the bar 23 returns to its closed position the bore through the tubing 16 is closed before the bore through the tubing 15.

The pressure switch 12 is arranged so that once it is switched on by an increase in the back-pressure upstream from the nozzle 3 it tends to remain in this position until the detector is reset. This feature is of particular importance where the further pinch valve 13 is not incorporated in the detector. The pressure switch 12 includes a frame 29 having a right angled cross-section, a collapsible bag 30, a strip of springy material 31 and an electrical microswitch 32. The microswitch 32 is of the type in which the axial position of its plunger at which the contacts are closed, is different from the axial position of its plunger at which the contacts are re-opened. The switch also includes a screw 33 the position of which is adjustable. The collapsible bag 30 is connected to the inlet of the pressure switch from the tubing upstream from the nozzle 3 and as the pressure within the bag 30 increases it urges the strip 31 away from the base of the frame. Initially the movement of the bag is only lightly restrained since the strip is fixed at its end 34. As the pressure within the bag 30 increases further, the strip moves into contact with the screw 33. As the pressure upstream from the nozzle 3 is increased the movement of the bag 30 is more strongly restrained as the strip 31 is in contact with the screw 33 and the leverage of the bag against the spring is reduced. When the plunger has moved into the position shown in dotted lines on FIG. 4 the contacts within the microswitch 32 are closed. As the pressure within the bag 30 reduces the contacts will remain closed until the spring 31 returns to the position shown in solid lines in FIG. 4, that is as it moves out of contact with the adjustable screw 33. Thus the bag 30 must collapse almost completely before the contacts on the microswitch 32 open once again. The pressure switch thus is made to operate through a large and adjustable pressure differential.

In this example an increase in pressure within the bag 30 from 0 to 5 inches water gauge moves the spring 31 from its rest position into contact with the adjustable screw 33. A further increase in pressure from 5 inches to 20 inches is required to move the free end of the spring 31 a distance equal to its initial movement to close the contacts on the microswitch 32. Thus a drop of pressure within the bag 30 of 15 inches water gauge is also required before the contacts on the switch 32 open once again. Thus the contacts of the pressure switch will close when the pressure is 20 inches water gauge but only re-open when the pressure falls below 5 inches water gauge.

The contacts of the microswitch 32 are connected in an external alarm circuit which is arranged to trigger an audible or visual alarm when the contacts are closed. This alarm will give an indication that the concentration of carbon dioxide in the cellar has reached a dangerous level.

Alternatively, a pressure switch with a very small differential pressure adjustment may be used in conjunction with an electrical switching device, such as a relay, to maintain the alarm condition once it has been triggered by a predetermined increase in pressure in the switch.

Figure 5:
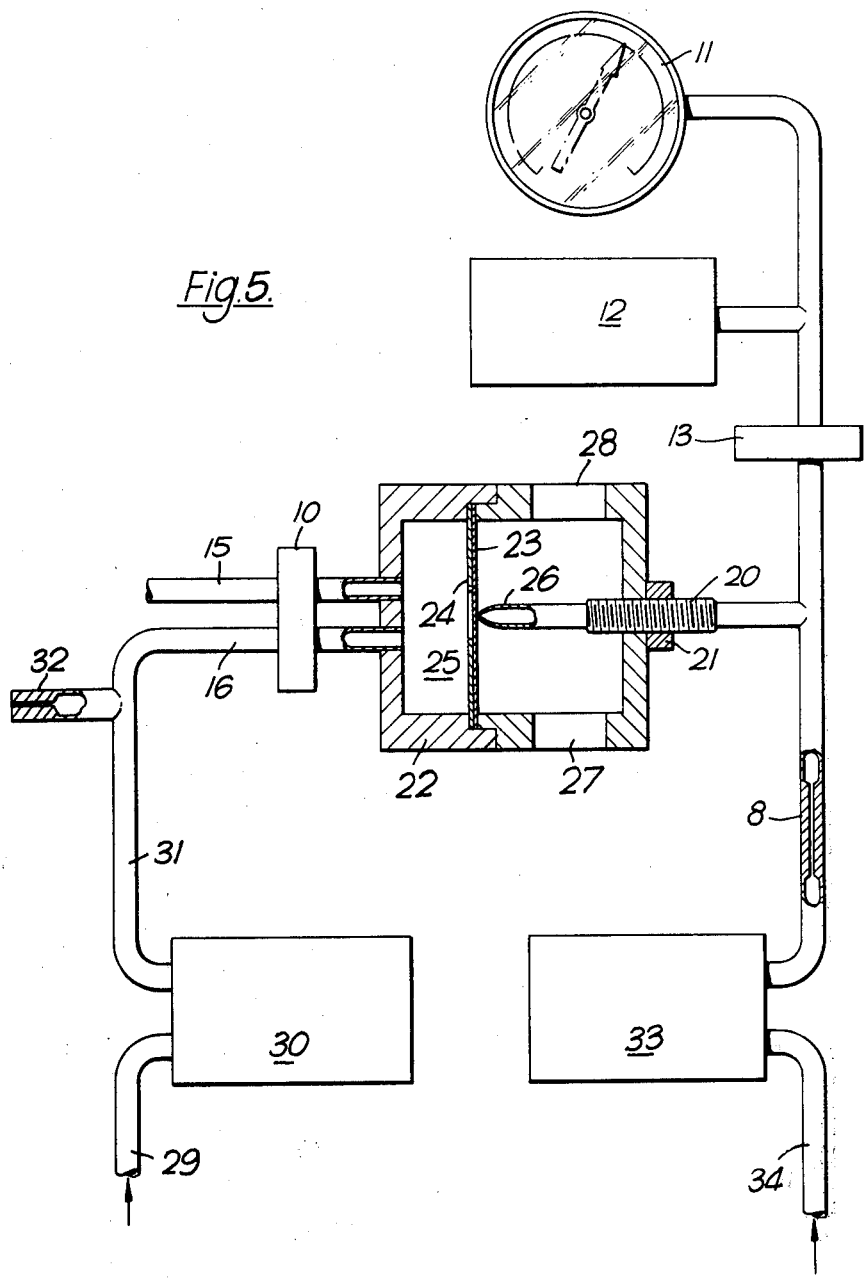

The second example of the detector shown particularly in FIG. 5 is generally similar to the first example but this second example works the other way round in that the sample of gas to be examined is introduced into the space and when the particular gas is present in the mixture of gases the gas permeates through the membrane, out of the space, to reduce the pressure within the space and cause the diaphragm to move inwards into the space. The arrangement of the pinch valves 10 and 13, the pressure gauge 11 and the pressure switch 12 are all substantially identical to those described with reference to the first example, and have been given similar reference numerals. This example is also primarily intended for collecting a sample of gas from a cellar, or other store containing carbonated beverages and examining it with regard to the concentration of carbon dioxide to ensure that it is safe for personnel to enter the cellar or store.

This second example of detector comprises a housing 22 containing a silicone rubber membrane 23 which is supported on a relatively rigid porous support 24. The silicone rubber membrane has a thickness of the order of 0.002 inch and the rigid porous support is formed by an annular ring of porous material and a ring having radially extending fingers extending inwards from its periphery. Thus it is identical with that shown and described fully in the first example except that the relatively rigid porous support 24 is on the other side of the membrane when compared to the first example.

The housing 22 and the membrane 24 bound and define a chamber 25. This chamber 25 forms the space which is partly bounded by the diaphragm and the membrane 23 and the pair of pinch valves 10 lead into the chamber 25 and form an inlet and an outlet for the chamber 25. A nozzle 26 is arranged adjacent the middle of the central unsupported region of the membrane 24 and arranged so that when the pressure inside the chamber 25 is the same as that outside, the nozzle 26 is adjacent the membrane 23 so that the membrane 23 interferes with any flow through the nozzle 26. The nozzle 26 is supported by the housing 22 and vents 27 and 28 are provided in the wall of the housing 22 to allow a free flow of gas to take place inside this part of the housing 22.

A sample of the mixture of the gases to be examined is drawn through an inlet tube 29 by a pump 30. The inlet tube 29 leads from a region from which the particular gas is most likely to be collected, and in this case, from the floor of the cellar or store. Again the detector is usually mounted outside the cellar. The outlet from the pump 30 leads through a further tube 31 to a bleed vent 32 and thence to the tubing 16 leading to the inlet of the pinch valves 10. The bleed 32 is provided to ensure that a healthy flow of gas is continuously drawn from the region to be sampled even when the pinch valves 10 are closed.

A second pump 33 draws a reference gas through its inlet 34. In this case the reference gas is fresh air taken from inside the detector casing as the detector is mounted outside the cellar or store. The reference gas may be taken from another position remote from the inlet to the sample tube 29 or it may be taken from a supply of a reference gas or mixture of gases. The pump 33 delivers the reference gas through a restriction 8 to the nozzle 26.

When the concentration of the particular gas, which in this case is carbon dioxide, in the chamber 25 is greater than the concentration of carbon dioxide on the other side of the membrane 23, the carbon dioxide from within the chamber 25 permeates through the membrane 23 at a rate that is faster than that of the carbon dioxide from the atmosphere outside the chamber 25 through the membrane 23 and into the chamber 25. Accordingly there is a net flow of carbon dioxide from the chamber 25 through the membrane 23 and into the atmosphere surrounding the chamber 25. This causes a drop of pressure inside the chamber 25 and causes the unsupported central region of the membrane 23 to bow inwards into the chamber 25. This movement of the membrane 23 away from the nozzle 26 reduces the interference of the membrane 23 on the flow of gas through the nozzle 26 and accordingly leads to a drop of pressure upstream from the nozzle 26. This causes the pressure gauge 11 to indicate a lower reading than the predetermined pressure and causes the electrical, pressure-responsive switch 12 to change its state. The switch 16 can be used to trigger an alarm circuit to give an indication that the concentration of carbon dioxide in the cellar or store is greater than that normally present in the atmosphere.

The pinch valves 10 are operated by a cam mechanism, similar to that described in the first example and thus they are opened regularly at predetermined intervals to introduce a fresh sample of gas from the region to be sampled into the chamber 25. In this way a sample of the gases present in the region to be sampled is taken at the predetermined timed intervals.

While the invention has been described and shown with particular reference to the preferred embodiments, it will be apparent that variations may be possible that would fall within the scope of the present invention, which is not intended to be limited except as defined in the following claims.

We claim:

1. A detector for detecting the presence of a particular gas in a mixture of gases, a membrane having two faces permeable by said particular gas at a rate greater than the other gases in said mixture, a thin flexible diaphragm and wall means, said membrane, said diaphragm and said wall means defining an enclosed space, said detector also including a nozzle to which, in use, a gas is supplied at a steady pressure, said nozzle having an opening at one end in proximity to said diaphragm so that movement of said thin flexible diaphragm interferes directly with the flow of said gas through said nozzle, and means for supplying said mixture of gases to one face of said membrane, the arrangement being such that when said particular gas is present in said mixture of gases said particular gas permeates through said membrane from said one face to change the pressure in said enclosed space causing said diaphragm to move to interfere with the flow through said nozzle and thereby produce a change of pressure in said supply of gas upstream from said nozzle, whereby said change in pressure constitutes a pneumatic signal indicating the presence of said particular gas in said mixture of gases.

2. The detector of claim 1, wherein said supply means includes a chamber, said one face of said membrane partly bounding said chamber and said chamber having an inlet for said mixture of gases and a vent outlet, whereby said mixture of gases floods said chamber.

3. The detector of claim 2, wherein said membrane is flexible, wherein said thin flexible diaphragm and said membrane are formed by the same piece of material, wherein said nozzle forms at least part of said inlet into said chamber, and wherein said supply means supplies said mixture of gases at a steady pressure to said nozzle.

4. The detector of claim 3, wherein said nozzle is adjacent said one face of said membrane and said mixture of gases supplied by said nozzle impinges directly on said membrane whereby when said particular gas is present in said mixture of gases said particular gas permeates through said combined membrane and diaphragm to increase the pressure within said enclosed space to cause said combined membrane and diaphragm to bow outwards away from said enclosed space and interfere directly with said flow of said mixture of gases through said nozzle.

5. The detector of claim 2, wherein said enclosed space includes inlet means having an inlet valve and outlet means having an outlet valve thereby allowing said enclosed space to be purged by a supply of gas being passed through it, said valves being arranged to isolate said space subsequently.

6. The detector of claim 4, wherein said enclosed space includes inlet means having an inlet valve and outlet means having an outlet valve thereby allowing said enclosed space to be purged by a supply of gas being passed through it, said valves being arranged to isolate said space subsequently.

7. The detector of claim 6, which further includes a timing device arranged to control said inlet and outlet valves of said enclosed space to purge said space at predetermined intervals.

8. The detector of claim 7, wherein said inlet and said outlet valves of said space are arranged whereby, in each purge cycle first said outlet valve is opened, then said inlet valve is opened to allow said purging gas to pass through said space and out of said outlet valve, then said inlet valve is closed, and finally said outlet valve is closed.

9. The detector of claim 8, which further includes at least one pressure-responsive device located upstream from said nozzle, said at least one device responding to an increase in said pressure of said mixture of gases upstream from said nozzle when said nozzle is throttled.

10. The detector of claim 9, including a further valve arranged to isolate said at least one device, said further valve being arranged to open before said outlet valve of said space is opened and to close once again immediately before said outlet valve of said space is opened, whereby said further valve maintains said at least one device in a pressurised state during the following cycle of said timing device and then allows said at least one device to be readjusted at the end of said following cycle.

11. The detector of claim 10, wherein said inlet and outlet valves of said space are formed by a pair of pinch valves comprising a pair of flexible tubes both of which are arranged to be closed by a common pivoted closure member, said inlet tubing being closer to the pivot of said closure member than said outlet tubing, whereby as said closure member moves towards or away from said tubing to pinch-off or open up the bore through said tubing, said inlet is opened after said outlet and closed before said outlet.

12. The detector of claim 9, wherein said pressure-responsive device is a pressure-responsive electrical switch.

13. The detector of claim 9, wherein said pressure-responsive device is a pressure gauge.

14. The detector of claim 1, wherein said supply means includes a valve-controlled inlet and outlet of said enclosed space to allow a sample of the mixture of gases to be introduced into said enclosed space, whereby when said particular gas is present in said mixture, said particular gas permeates through said membrane from said one side, out of said space to reduce said pressure in said space and cause said diaphragm to bow inwards into said space and produce a change in pressure in said supply of gas upstream from said nozzle.

15. The detector of claim 14, wherein said thin flexible diaphragm is arranged to interfere directly with said flow of said gas through said nozzle.

16. The detector of claim 15, wherein said membrane is flexible and wherein said thin flexible diaphragm and said membrane are both formed by the same piece of material.

17. The detector of claim 16, which further includes a timing device arranged to control said valve controlled inlet and outlet of said enclosed space to introduce a fresh sample into said space at predetermined intervals.

18. The detector of claim 17, wherein said valve controlled inlet and outlet of said space are arranged whereby, in each cycle first said outlet valve is opened, then said inlet valve is opened to allow said sample gas to pass through said space and out of said outlet valve, then said inlet valve is closed, and finally said outlet valve is closed.

19. The detector of claim 18, which further includes at least one pressure-responsive device located upstream from said nozzle, said at least one device responding to an increase in said pressure of said gas upstream from said nozzle.

20. The detector of claim 19, including a further valve arranged to isolate said at least one device, said further valve being arranged to open before said outlet valve of said space is opened and to close once again immediately before said outlet valve of said space is opened, whereby said further valve maintains said at least one device in a pressurised state during the following cycle of said timing device and then allows said at least one device to be readjusted at the end of said following cycle.

21. The detector of claim 20, wherein said inlet and outlet valves of said space are formed by a pair of pinch valves comprising a pair of flexible tubes both of which are arranged to be closed by a common pivoted closure member, said inlet tubing being closer to the pivot of said closure member than said outlet tubing, whereby as said closure member moves towards or away from said tubing to pinch-off or open up the bore through said tubing, said inlet is opened after said outlet and closed before said outlet.

22. The detector of claim 19, wherein said pressure-responsive device is a pressure-responsive electrical switch.

23. The detector of claim 19, wherein said pressure-responsive device is a pressure gauge.

24. A detector for detecting the presence of a particular gas in a mixture of gases including a membrane which is flexible, preferentially permeable by said particular gas and which has two faces, a thin flexible diaphragm and wall means, said membrane and said diaphragm being formed by the same piece of material and together with said walls means defining an enclosed space, said detector also including a nozzle to which, in use, a gas is supplied at a steady pressure, movement of said combined membrane and diaphragm being arranged to control flow through said nozzle, supply means to supply said mixture of gases to one face of said membrane and at least one pressure-responsive device located upstream from said nozzle wherein said supply means includes a chamber, said one face of said membrane partly bounding said chamber and said chamber having an inlet for said mixture of gases and a vent outlet and wherein said nozzle forms at least part of said inlet into said chamber and is adjacent to said one face and said mixture of gases supplied by said nozzle impinges directly on said membrane, whereby said mixture of gases floods said chamber, and further wherein said inlet has an inlet valve and said outlet has an outlet valve thereby allowing said enclosed space to be purged by a supply of gas being passed through it, said valves being arranged to isolate said space subsequently, the operation of said valves being controlled by a timing device so as to effect said purging at predetermined intervals, wherein said inlet and said outlet valves of said space are arranged whereby, in each purge cycle first said outlet valve is opened, then said inlet valve is opened to allow said purging as to pass through said space and out of said outlet valve, then said inlet valve is closed, and finally said outlet valve is closed, and also including a further valve arranged to isolate said at least one device, said further valve being arranged to open before said outlet valve of said space is opened and to close once again immediately before said outlet valve of said space is opened, whereby said further valve maintains said at least one device in a pressurized state during the following cycle of said timing device and then allows said at least one device to be readjusted at the end of said following cycle, the arrangement being such that, when said particular gas is present in said mixture of gases, said particular gas permeates through said combined membrane and diaphragm from said one face to increase the pressure in said enclosed space and cause said combined membrane and diaphragm to bow outwards away from said enclosed space and throttle said flow of said mixture of gases through said nozzle, thereby producing an increase in pressure, in said supply of gas upstream from said nozzle, said at least one device responding to said increase in pressure, thereby constitutes a pneumatic signal indicating the presence of said particular gas in said mixture of gases.

25. The detector of claim 24, wherein said inlet and outlet valves of said space are formed by a pair of pinch valves comprising a pair of flexible tubes both of which are arranged to be closed by a common pivoted closure member, said inlet tubing being closer to the pivot of said closure member than said outlet tubing, whereby as said closure member moves towards or away from said tubing to pinch-off or open up the bore through said tubing, said inlet is opened after said outlet and closed before said outlet.

26. A detector for detecting the presence of a particular gas in a mixture of gases including a membrane which is flexible, preferentially permeable by said particular gas and which has two faces, a thin flexible diaphragm and wall means, said membrane and said diaphragm being formed by the same piece of material and together with said wall means defining an enclosed space, said detector also including a nozzle to which, in use, a gas is supplied at a steady pressure, movement of said combined membrane and diaphragm being arranged to control flow through said nozzle, supply means to supply and at least one pressure-responsive device, located upstream from said nozzle wherein said combined membrane and diaphragm are normally arranged to interfere directly with said flow of said gas through said nozzle, and wherein said supply means includes a valve-controlled inlet and outlet of said enclosed space to allow a sample of the mixture of gases to be introduced into said enclosed space, said inlet and outlet being controlled by a timing device so that a fresh sample is introduced into said space at predetermined intervals, said timing device being set so that in each cycle first said outlet valve is opened, then said inlet valve is opened to allow said sample gas to pass through said space and out of said outlet valve, then said inlet valve is closed, and finally said outlet valve is closed, and also including a further valve arranged to isolate said at least one device, said further valve being arranged to open before said outlet valve of said space is opened and to close once again immediately before said outlet valve of said space is opened, whereby said further valve maintains said at least one device in pressurized state during the following cycle of said timing device and then allows said at least one device to be readjusted at the end of said following cycle, whereby, when said particular gas is present in said mixture, said particular gas permeates through said combined membrane and diaphragm from said one side and out of said space to reduce said pressure in said space and cause said diaphragm to bow inwards into said space and produce a decrease in pressure in said supply of gas upstream from said nozzle, said at least one device responding to said decrease in said pressure, thereby constituting a pneumatic signal indicating the presence of said particular gas in said mixture of gases.

27. The detector of claim 26, wherein said inlet and outlet valves of said space are formed by a pair of pinch vales comprising a pair of flexible tubes both of which are arranged to be closed by a common pivoted closure member, said inlet tubing being closer to the pivot of said closure member than said outlet tubing, whereby as said closure member moves towards or away from said tubing to pinch-off or open up the bore through said tubing, said inlet is opened after said outlet and closed before said outlet.

* * * * *